US009075790B2

(12) United States Patent
Chan et al.

(10) Patent No.: US 9,075,790 B2
(45) Date of Patent: Jul. 7, 2015

(54) INTERNAL FOCUS REFERENCE BEADS FOR IMAGING CYTOMETRY (75) Inventors: Leo L. Chan, North Andover, MA (US);
Jean Qiu, North Andover, MA (US);
Peter Li, North Andover, MA (US);
Kevin Flanagan, Lawrence, MA (US);
Timothy Smith, Lawrence, MA (US)

(73) Assignee: Nexcelom Bioscience LLC, Lawrence, MA (US)

( * ) Notice: Subject to any disclaimer, the term of this patent is extended or adjusted under 35 U.S.C. 154(b) by 257 days.

(21) Appl. No.: 13/878,618

(22) PCT Filed: Oct. 20, 2011

(86) PCT No.: PCT/US2011/057177
§ 371 (c)(1),
(2), (4) Date: Sep. 4, 2013

(87) PCT Pub. No.: WO2012/054783
PCT Pub. Date: Apr. 26, 2012

(65) Prior Publication Data
US 2013/0336567 A1 Dec. 19, 2013

Related U.S. Application Data (60) Provisional application No. 61/405,479, filed on Oct. 21, 2010.

(51) Int. Cl.
G06K 9/00 (2006.01)
G06F 19/26 (2011.01)
G01N 21/64 (2006.01)

(52) U.S. Cl.
CPC ............ *G06F 19/26* (2013.01); *G01N 21/6428* (2013.01); *G01N 21/6456* (2013.01); *G01N 21/6486* (2013.01)

(58) Field of Classification Search
USPC .................................................. 382/128–134
See application file for complete search history.

(56) References Cited

U.S. PATENT DOCUMENTS

| 4,767,206 A * | 8/1988 | Schwartz ........................ 356/73 |
| 4,850,024 A * | 7/1989 | Motoike et al. ............... 382/134 |
| 5,741,213 A * | 4/1998 | Kouchi et al. ................. 600/310 |
| 2005/0152593 A1* | 7/2005 | Calvin ......................... 382/133 |
| 2008/0019584 A1* | 1/2008 | Lindberg et al. ............. 382/134 |
| 2010/0285594 A1* | 11/2010 | Purvis, Jr. ...................... 436/10 |
| 2011/0066385 A1* | 3/2011 | Rajwa et al. ................... 702/19 |
| 2013/0109050 A1* | 5/2013 | Purvis, Jr. ...................... 435/34 |
| 2013/0336567 A1* | 12/2013 | Chan et al. .................... 382/133 |

* cited by examiner

Primary Examiner — Alex Liew
(74) Attorney, Agent, or Firm — Milstein Zhang & Wu LLC (57) ABSTRACT The invention generally relates to analytical and monitoring systems useful for analyzing and measuring cells and biological samples. More particularly, the invention provides systems and methods for internal calibration and focus reference for cytometry imaging.

18 Claims, 8 Drawing Sheets

Turn UV light on and detect beads for focusing

Turn blue light on and detect total particles (WBC + beads)

INTERNAL FOCUS REFERENCE BEADS FOR IMAGING CYTOMETRY

PRIORITY CLAIMS AND RELATED APPLICATIONS

This application claims the benefit of priority from PCT/US11/57177, filed Oct. 20, 2011, which claims the benefit of priority from U.S. Provisional Application Ser. No. 61/405,479, filed Oct. 21, 2010, the entire content of each of which is incorporated herein by reference for all purposes.

TECHNICAL FIELDS OF THE INVENTION

The invention generally relates to analytical and monitoring systems useful for analyzing and measuring cells and biological samples. More particularly, the invention relates to systems and methods for internal calibration and focus reference for imaging cytometry.

BACKGROUND OF THE INVENTION

An important aspect in the fields of medical diagnostics and biomedical research involves detection, identification, quantification, and characterization of various cells and biomolecules of interest through testing of biological samples such as blood, spinal fluid, cell culture and urine. Healthcare providers and biomedical researchers routinely analyze such biological samples for the microscopic presence and concentrations of cells and biomolecules.

For example, there is a need for validating the number of leukocytes (i.e. white blood cells) in a patient blood sample for blood transfusion qualification. By using an imaging cytometry method (Cellometer, Nexcelom Bioscience, LLC), leukocyte cell count can be measured by imaging a large area of a thin chamber, which allows counting of all the leukocytes within a specific scanned volume. Whole blood contains a high concentration of red blood cells, which often prevent the leukocytes from being seen by naked eyes, unless the red blood cells are lysed or a fluorescence method is used that specifically stains the leukocytes. With the detection methods mentioned above, the leukoreduction qualifying personnel would be able to focus on the leukocytes either using fluorescence or bright-field when red blood cells are lysed. However, most of the leukoreduced patient blood samples contain very low concentration of leukocytes; therefore, an imaging system may not be able to detect any presence of leukocytes, which means there is no object to focus on in the image field.

Therefore, a long-felt need exists for systems and methods that provide simple and accurate calibration and internal references for focusing and quality control so as to allow accurate and rapid imaging and measurement of ultralow concentration samples.

SUMMARY OF THE INVENTION

The invention is based a unique design approach resulting in a much improved system for calibrating and internal focusing in imaging cytometry. The invention provides improvements in measuring, analyzing, counting, or monitoring microscopic objects such as biological cells of various types. In particular, the system allows more accurate detection and measurement of cells at extremely low concentrations. This novel approach enables effective and efficient internal focus and referencing for confirmation of low concentration leukoreduced blood sample cell count and significantly improve the detection limits and confidence on the results obtained from imaging cytometry.

In one aspect, the invention generally relates to a method for determining the presence or concentration of target cells in a sample. The method includes: mixing a sample to be tested for the presence or concentration of target cells with a pre-determined amount of micro-particles, wherein the target cells are capable of fluorescent emission at a first detection wavelength upon excitation at a first excitation wavelength, and wherein the microparticles are capable of fluorescent emission at a second detection wavelength upon excitation at a second excitation wavelength; loading the sample into a sample chamber of a fluorescent imaging system; directing a light beam at the sample, wherein the light beam comprising the second excitation wavelength; acquiring a fluorescent image of the sample at the second detection wavelength; calibrating the fluorescent imaging system with the fluorescent image acquired at the second detection wavelength; directing a second light beam at the sample, wherein the second light beam comprising the first excitation wavelength; acquiring a fluorescent image of the sample at the first detection wavelength; and determining the presence or concentration of the target cells in the sample.

In another aspect, the invention generally relates to a method for calibrating a fluorescent imaging system useful for measuring target cells at low concentrations. The method includes: preparing a sample comprising a pre-determined amount of micro-particles having associated thereon a dye capable of fluorescent emission; directing a light beam at the sample, wherein the light beam comprises a wavelength capable of fluorescent excitation of the dye, thereby resulting in an observable fluorescent image of the micro-particles; and calibrating the fluorescent imaging system with the observable fluorescent image of the micro-particles as references.

In yet another aspect, the invention generally relates to a method for detecting the presence of a biological material in a sample. The method includes: staining a sample to be tested for the presence of the biological material with a dye capable of fluorescent emission at a detection wavelength upon excitation at a excitation wavelength; mixing the sample to be tested with a pre-determined amount of micro-particles capable of fluorescent emission both at the detection wavelength and at a reference wavelength upon excitation at the excitation wavelength; acquiring a fluorescent image of the sample at the reference wavelength; acquiring a fluorescent image of the sample at the detection wavelength; and determining the presence of the biological material in the sample.

DETAILED DESCRIPTION OF THE INVENTION

The invention provides a unique design approach and a much improved system for calibrating and internal focusing in imaging cytometry. In particular, the invention provides improvements in measuring, analyzing, counting, or monitoring microscopic objects such as biological cells of various types. The system of the invention allows more accurate detection and measurement of cells at extremely low concentrations. This novel approach significantly lowers the detection limits and increases the confidence on the results obtained from imaging cytometry.

The biological mechanisms of many diseases have been clarified by microscopic examination of tissue samples or body fluids. Histopathological examination has also permitted the development of effective medical treatments for a variety of illnesses. In standard anatomical pathology, a diagnosis is made on the basis of cell morphology and staining characteristics. Microscopic examination and classification of tissue samples stained by standard methods (such as hematoxylin and eosin) have improved cancer treatment significantly. Tumor samples, for example, can be examined to characterize the tumor type and indicate whether the patient will likely to respond to a particular form of chemotherapy.

Traditionally, fluorescence detection for cell-based assays is performed using fluorescence microscopy, fluorescent plate reader, or flow cytometry. These fluorescence detection methods usually incorporate expensive excitation light sources such as lasers or arc lamps in order to have high intensity excitation. In general, there is an excitation light source and a detection probe with an emission filter to pick up specific fluorescent signals. In an instrument such as fluorescent microscope, it often requires a dichroic filter to reflect the light from the top normally incident to the target biosamples. The emitted fluorescence then is picked up by passing through the dichroic filter into the detector (camera, spectrometer, etc.).

Figure 1:
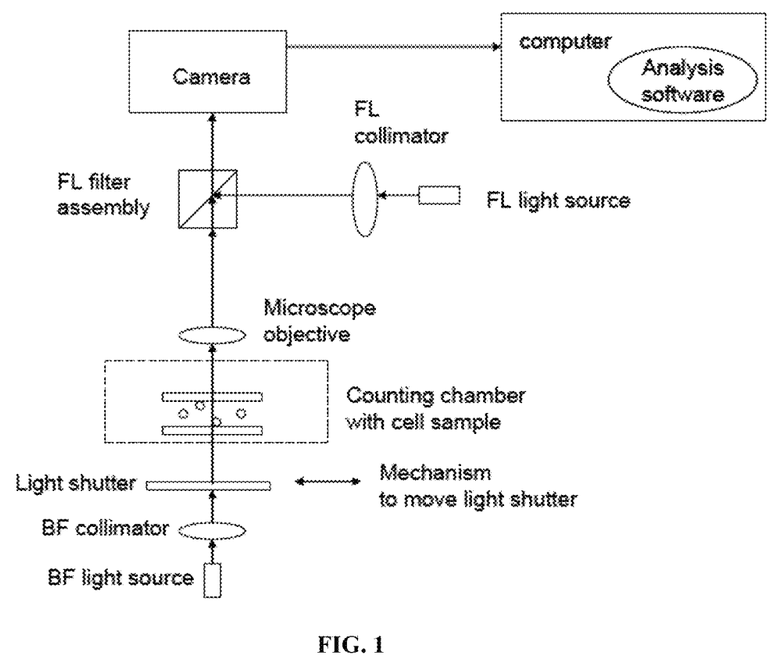
FIG. 1 shows an exemplary prior art cell counting system.

Previously, the Nexcelom Bioscience fluorescent Cellometer technology utilized a filter cube provided by Omega Optical in an assembly with optics, camera, and sample holder. It was able to provide sufficient fluorescent images of cells and other biosamples (FIG. 1). The technology provided a simple and efficient method to generate fluorescent images of biological samples, but lacked the sensitivity for low fluorescent signal detection. One attributed factor was the leaking of excitation light through the emission filter in the filter cube. In addition, the filter cube format was not very flexible in color selection. Only one specific filter cube and one LED could be used for one color, there was not much room to incorporate other colors.

As disclosed herein, in an embodiment of the invention fluorescent microspheres are utilized to develop a simple internal focusing and calibration method for low concentration leukoreduced blood sample. The current fluorescence detection method of leukocytes is staining with Acridine Orange (AO) nucleic acid dye and excitation/emission using wavelengths at 480 nm/525 nm. By using fluorescent microspheres that can be excited at ultraviolet (UV) light and emits green fluorescence (525 nm), one can alternate excitation light source to detect the microspheres under UV excitation for focusing and then count the AO stained leukocytes under blue excitation.

The present invention significantly improves the sensitivity and the limit of detection.

In one aspect, the invention generally relates to a method for determining the presence or concentration of target cells in a sample. The method includes: mixing a sample to be tested for the presence or concentration of target cells with a pre-determined amount of micro-particles, wherein the target cells are capable of fluorescent emission at a first detection wavelength upon excitation at a first excitation wavelength, and wherein the microparticles are capable of fluorescent emission at a second detection wavelength upon excitation at a second excitation wavelength; loading the sample into a sample chamber of a fluorescent imaging system; directing a light beam at the sample, wherein the light beam comprising the second excitation wavelength; acquiring a fluorescent image of the sample at the second detection wavelength; calibrating the fluorescent imaging system with the fluorescent image acquired at the second detection wavelength; directing a second light beam at the sample, wherein the second light beam comprising the first excitation wavelength; acquiring a fluorescent image of the sample at the first detection wavelength; and determining the presence or concentration of the target cells in the sample.

In some embodiments, the target cells are capable of fluorescent without staining with a dye. In some other embodiments, the target cells are capable of fluorescent only with staining with a dye.

In some embodiments, the microparticles are capable of fluorescent without staining with a dye. In some other embodiments, the microparticles are capable of fluorescent only with staining with a dye.

In certain preferred embodiments, the target cells are stained with a first dye capable of fluorescent emission at a first detection wavelength upon excitation at a first excitation wavelength, and the microparticles are stained with a second dye a second dye capable of fluorescent emission at a second detection wavelength upon excitation at a second excitation wavelength.

In certain embodiments, the method includes staining a sample to be tested for the presence or concentration of target cells with a first dye, wherein the first dye is capable of fluorescent emission at a first detection wavelength upon excitation at a first excitation wavelength; and mixing the sample to be tested with a pre-determined amount of microparticles having associated thereon a second dye capable of fluorescent emission at a second detection wavelength upon excitation at a second excitation wavelength.

In some preferred embodiments, the micro-particles having associated thereon a second dye are capable of fluorescent emission at the first detection wavelength upon excitation at a second excitation wavelength. And determining the presence or concentration of the target cells in the sample includes comparing the fluorescent image of the sample obtained at the second detection wavelength and the fluorescent image of the sample obtained at the first detection wavelength.

In certain embodiments, calibrating the fluorescent imaging system includes focusing the fluorescent imaging system on the micro-particles as references.

The sample to be tested may have less than about $10^8$ cells/ml of the target cells (e.g., less than about $10^7$ cells/ml, less than about $10^6$ cells/ml, less than about $10^5$ cells/ml, less than about $10^4$ cells/ml, less than about $10^3$ cells/ml, or less than about $10^2$ cells/ml of the target cells). In certain embodiments, the sample to be tested consists of a single target cell in the fluorescent image acquired at the first detection wavelength.

Samples that may be analyzed using the methods of the invention include biological materials obtained from or derived from living organisms. Such samples include, but are not limited to, hair, skin, tissue, cultured cells, cultured cell media, and body fluids. The target cells may be any cells that are suitable for detection and measurement by the methods of the invention, for example, leukocytes, stem cells, spinal cells, synovial, cells of body fluids, milk somatic cells, and immunophenotyping.

In certain preferred embodiments, the micro-particles are microspheres, for example, selected from various fluorescence wavelengths of polystyrene, poly methyl methacrylate beads.

In some embodiments, the microspheres may have substantially uniform diameters, for example, from about 3 μm to about 50 μm in diameters, from about 4 μm to about 30 μm in diameters, or from about 5 μm to about 15 μm in diameters.

The first dye may be selected from any dyes suitable for particular applications, for example, acridine orange, propidium iodide (PI), and ethidium bromide.

The second dye may be selected from any stains capable of excitation at UV wavelength and fluorescence emission at green fluorescence, for example, ProQ Emerald 300 or Firefli fluorescent green dye.

In some embodiments, the first excitation wavelength is selected from about 470 nm to about 550 nm, for example, selected from about 480 nm to about 525 nm. In some embodiments, the second excitation wavelength is selected from about 350 nm to about 400 nm, for example, from about 375 nm to about 395 nm. In some other embodiments, the first excitation wavelength is selected from about 580 nm to about 650 nm, from about 590 nm to about 640 nm, from about 600 nm to about 630 nm. The second excitation wavelength is selected from about 470 nm to about 525 nm.

In some embodiments, the first detection wavelength is selected from about 500 nm to about 640 nm, for example, selected from about 510 nm to about 600 nm. In some embodiments, the second detection wavelength is the same as the first detection wavelength, for example, selected from about 510 nm to about 600 nm, from about 690 nm to about 750 nm, or from about 700 nm to about 740 nm.

In another aspect, the invention generally relates to a method for calibrating a fluorescent imaging system useful for measuring target cells at low concentrations. The method includes: preparing a sample comprising a pre-determined amount of micro-particles having associated thereon a dye capable of fluorescent emission; directing a light beam at the sample, wherein the light beam comprises a wavelength capable of fluorescent excitation of the dye, thereby resulting in an observable fluorescent image of the micro-particles; and calibrating the fluorescent imaging system with the observable fluorescent image of the micro-particles as references.

In some embodiments, calibrating the fluorescent imaging system includes properly focusing the fluorescent imaging system with the micro-particles as qualitative references.

In some other embodiments, calibrating the fluorescent imaging system comprises measuring one or more properties of the micro-particles as quantitative internal references, for example, the particle sizes and fluorescent intensities of the micro-particles.

In yet another aspect, the invention generally relates to a method for detecting the presence of a biological material in a sample. The method includes: staining a sample to be tested for the presence of the biological material with a dye capable of fluorescent emission at a detection wavelength upon excitation at a excitation wavelength; mixing the sample to be tested with a pre-determined amount of micro-particles capable of fluorescent emission both at the detection wavelength and at a reference wavelength upon excitation at the excitation wavelength; acquiring a fluorescent image of the sample at the reference wavelength; acquiring a fluorescent image of the sample at the detection wavelength; and determining the presence of the biological material in the sample.

EXAMPLES

Materials and Instrumentation

First, two types of microspheres were examined for developing internal focusing reference method. Both microspheres can be excited at UV and emits at green wavelength. Microsphere #2 can also be excited at blue light and emits at green. The microspheres were measured under UV and blue excitation to observe its fluorescence output. A sample blood was taken from a subject by pricking his finger to obtain a small volume of blood. Acridine orange stain was prepared to 10 μg/ml for staining the leukocytes in the blood sample. The Cellometer Vision (Nexcelom) system is used in the development of the internal focus reference microspheres. The system contains two filter sets. One set has an excitation at UV range and emission at green, the other set has an excitation at blue range and the same green emission.

Initial Fluorescence Detection Measurement

First, twenty microliters of blood sample was stained with 5 μl of AO to observe its fluorescence under both UV and blue excitation with a green emission filter. The stained blood (20 μl) was pipetted into a Cellometer counting chamber and the fluorescence was detected using the Cellometer Vision system. Next, the microspheres were pipetted into the chamber and their fluorescence was also measured in the system. Finally, the microspheres were mixed with AO and their fluorescence is measured again the system.

Internal Focus Reference Method

The appropriate microspheres selected from the previous experiment were mixed with AO stained blood sample. Twenty microliters of blood sample, 5 μl of AO, and 5 μl of microspheres were mixed. The mixture was pipetted into a Cellometer counting chamber and images were taken for leukocyte counting.

Initial Fluorescence Detection Measurement

Figure 2:
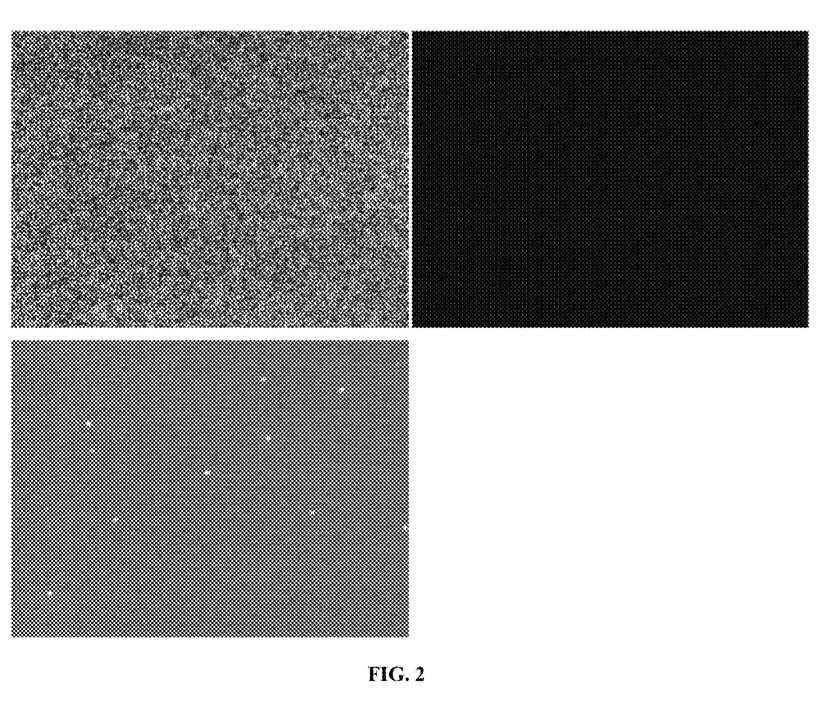
FIG. 2 shows (top left) a bright-field image of Acridine Orange (AO) stained blood sample; (top right) a stained sample under UV excitation, which resulted in no fluorescent signals; (bottom left) a stained sample under blue excitation, which resulted in bright fluorescence signal of AO stained leukocytes.

The fluorescent images of blood sample stained with AO are shown in FIG. 2. The fluorescent signal of AO stained leukocytes is high under blue excitation and there is no signal under UV excitation. The bright-field image is also shown in FIG. 2, where the red blood cells overwhelm the entire image, thus leukocytes can only be observed under fluorescence.

Figure 3:
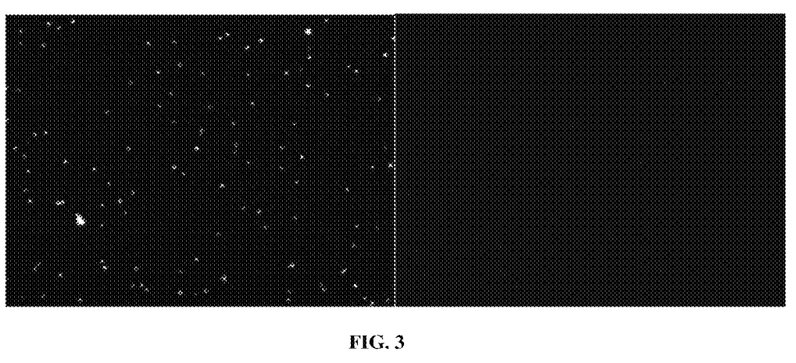
FIG. 3 shows (left) microspheres under UV excitation, which resulted in bright fluorescence signal; (right) microspheres under blue excitation, which resulted in no fluorescent signals.

The fluorescent images of microspheres are shown in FIG. 3. The fluorescent signal of the microspheres is high under UV excitation, and there is no signal under blue excitation as expected. The results suggest that the mixture of AO stained blood with microspheres can be used to focus the sample under UV channel and count only the AO stained leukocytes in the blue channel.

Figure 4:
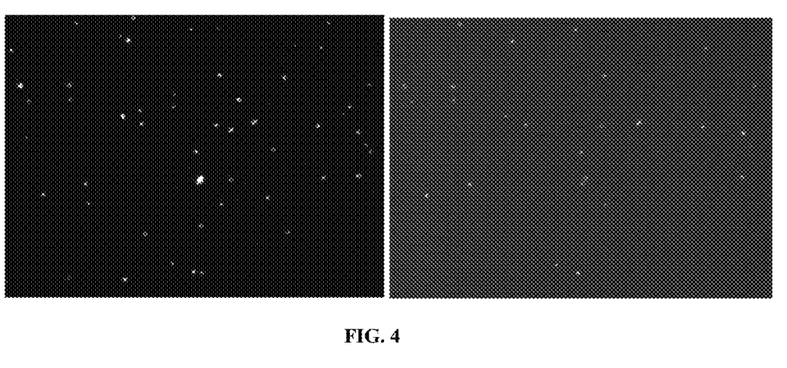
FIG. 4 shows (left) microspheres under UV excitation, which resulted in bright fluorescence signal; (right) microspheres stained with AO under blue excitation showing AO binding to the microspheres and emitting green fluorescence.

The fluorescent images of microspheres mixed with AO are shown in FIG. 4. The fluorescent signal of the microspheres is high under UV excitation as expected. However, in the blue channel, the AO bound to the microspheres and fluoresced under blue excitation. The microspheres were replaced with the second type mentioned earlier, which fluoresce under both excitation light source.

Internal Focus Reference Method

Figure 5:
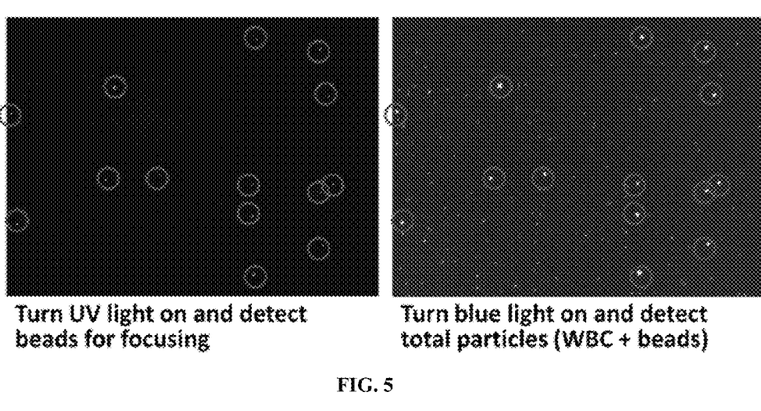
FIG. 5 shows (left) microspheres under UV excitation, which resulted in bright fluorescence signal; (right) microspheres and AO stained leukocytes under blue excitation showing AO bright fluorescence for both particles.

The fluorescent images of blood sample stained with AO mixed with microspheres are shown in FIG. 5. The fluorescent signal of the mixture showed only bright microsphere fluorescence under UV excitation, while both microspheres and AO stained leukocytes are high under blue excitation.

By identifying the microspheres under UV excitation channel and utilizing them to focus, the actual leukocytes can be counted in the blue channel by subtracting the microsphere counts from the total count in the blue channel. This method can be used when the concentration of leukocytes in the blood sample is extremely low, where only one or even no cells are detected. If this is the case, the focus reference microspheres can guarantee that the image is focused on to the focal plane of the objective, so that no discrepancy is raised when the leukoreduced blood samples are qualified.

Example 1

Imaging of Leukocytes

Using a large format camera, a large volume of blood was imaged, specifically for counting leukocytes for validating leukoreduced blood sample. Two images were captured (FIG. 6), one with excitation of UV and other with blue light. The blood sample was diluted 1 to 1 with Acridine Orange stain and fluorescent beads that fluoresces in both channels.

Figure 6:
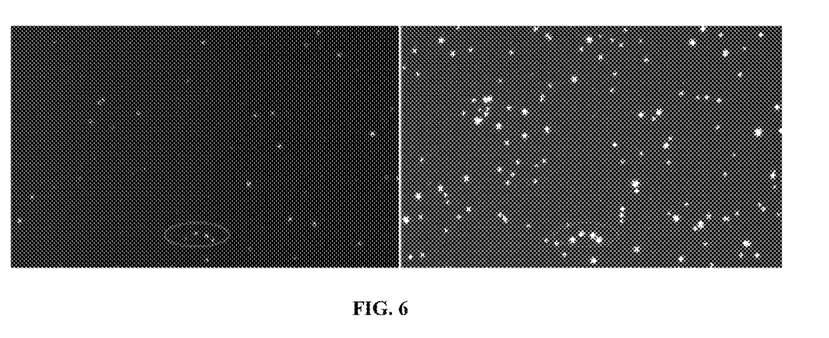
FIG. 6 shows (left) microspheres under UV excitation, which resulted in bright fluorescence signal; (right) microspheres and AO stained leukocytes under blue excitation showing AO bright fluorescence for both particles. The red line circles are the microspheres fluorescing in both channels.

Counting only the beads in the UV excitation channel and counting all the particles in the blue excitation channel (beads+AO stained leukocytes), a subtraction result in a measurement of the leukocyte concentration in the blood sample.

Example 2

Imaging of Leukocytes

Figure 7:
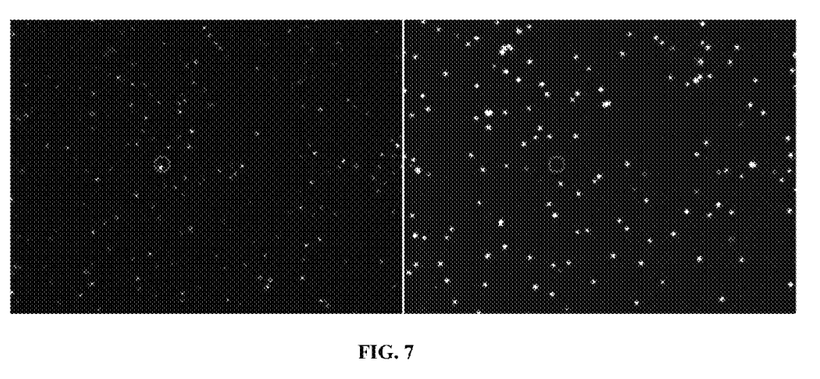
FIG. 7 shows microspheres under UV excitation, which resulted in bright fluorescence signal while PI stained Jurkat cells fluoresced slightly: (right) Only the PI stained Jurkat cells under blue excitation showed PI bright fluorescence. The red line circles are the microspheres fluorescing in both channels.
Figure 8:
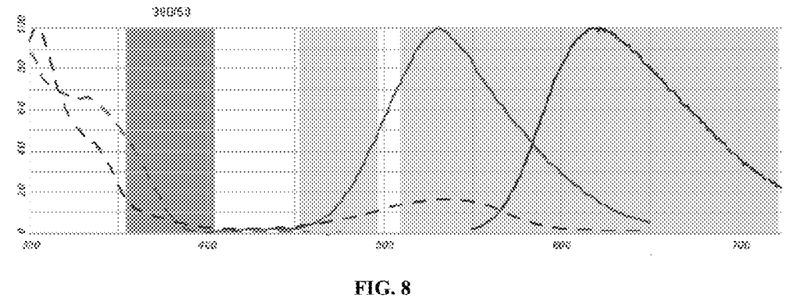
FIG. 8 shows excitation and emission spectra of UV excited beads (green) and propidium iodide (blue). The UV light excites both beads and PI stained Jurkat cells, and the long pass filter picks up both fluorescences, except that the Jurkats cells are much weaker. The blue light excites only PI; therefore, only Jurkat cells can be detected.

Using PI stained jurkat, with optical modules QMAX blue with 510 nm long pass filter, and 535 nm-401 nm with 510 nm long pass filter, two images were taken with UV and blue excitation (FIG. 7 and FIG. 8).

No fluorescence of beads was observed in the channel that detects PI stained Jurkats. Method would involve focusing under UV excitation, with beads, then switching to blue excitation and counting all the Cells stained with PI. This is a much simpler method than the previous described method, where a subtraction is not needed. The method is using one channel with beads to focus, and then switch to the other channel to count all the cells.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for determining the presence or concentration of target cells in a sample, comprising:
    mixing a sample to be tested for the presence or concentration of target cells with a pre-determined amount of micro-particles, wherein the target cells are capable of fluorescent emission at a first detection wavelength upon excitation at a first excitation wavelength, and wherein the microparticles are capable of fluorescent emission at a second detection wavelength upon excitation at a second excitation wavelength;
    loading the sample into a sample chamber of a fluorescent imaging system;
    directing a light beam at the sample, wherein the light beam comprising the second excitation wavelength;
    acquiring a fluorescent image of the sample at the second detection wavelength;
    calibrating the fluorescent imaging system with the fluorescent image acquired at the second detection wavelength;
    directing a second light beam at the sample, wherein the second light beam comprising the first excitation wavelength;
    acquiring a fluorescent image of the sample at the first detection wavelength; and
    determining the presence or concentration of the target cells in the sample.

2. The method of claim 1, wherein the target cells are capable of fluorescent without staining with a dye.

3. The method of claim 1, wherein the target cells are capable of fluorescent with staining with a dye.

4. The method of claim 1, wherein the microparticles are capable of fluorescent without staining with a dye.

5. The method of claim 1, wherein the microparticles cells are capable of fluorescent with staining with a dye.

6. The method of claim 1, wherein the target cells are stained with a first dye capable of fluorescent emission at a first detection wavelength upon excitation at a first excitation wavelength, and wherein the microparticles are stained with a second dye a second dye capable of fluorescent emission at a second detection wavelength upon excitation at a second excitation wavelength.

7. The method of claim 1, comprising
staining a sample to be tested for the presence or concentration of target cells with a first dye, wherein the first dye is capable of fluorescent emission at a first detection wavelength upon excitation at a first excitation wavelength; and
mixing the sample to be tested with a pre-determined amount of micro-particles having associated thereon a second dye capable of fluorescent emission at a second detection wavelength upon excitation at a second excitation wavelength.

8. The method of claim 6, wherein the micro-particles having associated thereon a second dye are capable of fluorescent emission at the first detection wavelength upon excitation at a second excitation wavelength, and
wherein determining the presence or concentration of the target cells in the sample comprising comparing the fluorescent image of the sample obtained at the second detection wavelength and the fluorescent image of the sample obtained at the first detection wavelength.

9. The method of claim 1, wherein calibrating the fluorescent imaging system comprises focusing the fluorescent imaging system on the micro-particles as references.

10. The method of claim 1, wherein the target cells are selected from the group consisting of: leukocytes, stem cells, spinal cells, synovial, cells of body fluids, milk somatic cells, and immunophenotyping.

11. The method of claim 1, wherein the micro-particles are microspheres.

12. The method of claim 1, wherein the micro-particles are selected from the group consisting of: various fluorescence wavelengths of polystyrene, poly methyl methacrylate beads.

13. The method of claim 1, wherein the first dye is selected from the group consisting of: acridine orange, propidium iodide, and ethidium bromide.

14. The method of claim 1, wherein the second dye is selected from stains capable of excitation at UV wavelength and fluorescence emission at green fluorescence.

15. The method of claim 1, wherein the second dye is ProQ Emerald 300 or Firefli fluorescent green dye.

16. The method of claim 1, wherein the first excitation wavelength is selected from about 470 nm to about 550 nm and the second excitation wavelength is selected from about 350 nm to about 400 nm.

17. The method of claim 1, wherein the first detection wavelength is selected from about 500 nm to about 640 nm.

18. The method of claim 1, wherein the second detection wavelength is the same as the first detection wavelength.

* * * * *